(12) United States Patent
Jenkins et al.

(10) Patent No.: US 8,653,272 B2
(45) Date of Patent: Feb. 18, 2014

(54) FUSED PYRIDINE DERIVATIVES AS KINASE INHIBITORS

(75) Inventors: Kerry Jenkins, Slough (GB); Christopher James Lock, Slough (GB); Andrew James Ratcliffe, Slough (GB)

(73) Assignee: UCB Pharma S.A., Brussels (BE)

( * ) Notice: Subject to any disclaimer, the term of this patent is extended or adjusted under 35 U.S.C. 154(b) by 241 days.

(21) Appl. No.: 13/124,947

(22) PCT Filed: Oct. 21, 2009

(86) PCT No.: PCT/GB2009/002504
§ 371 (c)(1), (2), (4) Date: Apr. 19, 2011

(87) PCT Pub. No.: WO2010/046639
PCT Pub. Date: Apr. 29, 2010

(65) Prior Publication Data
US 2011/0201630 A1 Aug. 18, 2011

(30) Foreign Application Priority Data
Oct. 24, 2008 (GB) .................................. 0819593.5

(51) Int. Cl.
*A61K 31/4365* (2006.01)
*C07D 417/02* (2006.01)

(52) U.S. Cl.
USPC .......................................... 546/113; 514/301

(58) Field of Classification Search
USPC ........................................... 514/301; 546/113
See application file for complete search history.

(56) References Cited

U.S. PATENT DOCUMENTS

2003/0236271 A1 12/2003 Hayakawa et al.
2005/0014771 A1 1/2005 Hayakawa et al.

FOREIGN PATENT DOCUMENTS

WO 2008/118455 A1 10/2008
WO 2008/118468 A1 10/2008

OTHER PUBLICATIONS

Michelotti et. al. "Two classes of p38a MAP kinase inhibitors having a common diphenylether core but exhibiting divergent binding modes" Bioorganic & Medicinal Chemistry Letters 2005, 15, 5274-5279.*
Jiang et. al. "3,5-Disubstituted quinolines as novel c-Jun N-terminal kinase inhibitors." Bioorganic & Medicinal Chemistry Letters 2007, 17, 6378-6382.*
Liu et. al. "Synthesis and SAR of 1,9-dihydro-9-hydroxypyrazolo[3,4-b]quinolin-4-ones as novel, selective c-Jun N-terminal kinase inhibitors" Bioorganic & Medicinal Chemistry Letters 2006, 16, 2590-2594.*
Miyazaki et. al. "Design and effective synthesis of novel templates, 3,7-diphenyl-4- amino-thieno and furo-[3,2-c]pyridines as protein kinase inhibitors and in vitro evaluation targeting angiogenetic kinases" Bioorganic & Medicinal Chemistry Letters 2007, 17, 250-254.*
Mulvihill et. al. "Novel 2-phenylquinolin-7-yl-derived imidazo[1,5-a]pyrazines as potent insulin-like growth factor-I receptor (IGF-IR) inhibitors" Bioorganic & Medicinal Chemistry 2008, 16, 1359-1375.*
Mulvihill et. al. "1,3-Disubstituted-imidazo[1,5-a]pyrazines as insulin-like growth-factor-I receptor (IGF-IR) inhibitors" Bioorganic & Medicinal Chemistry Letters 2007, 17, 1091-1097.*
Chowdhury et. al. "Discovery and optimization of indoles and 7-azaindoles as Rho kinase (ROCK) inhibitors (part-I)" Bioorg. Med. Chem. Lett. 21 (2011) 7107-7112.*

* cited by examiner

*Primary Examiner* — David K O Dell
(74) *Attorney, Agent, or Firm* — McDonnell Boehnen Hulbert & Berghoff LLP

(57) ABSTRACT

A series of heteroaryl-substituted fused pyridine derivatives, in particular heteroaryl-substituted thieno[3,2-6]pyridine derivatives, being selective inhibitors of PO kinase enzymes, are accordingly of benefit in medicine, for example in the treatment of inflammatory, autoimmune, cardiovascular, neurodegenerative, metabolic, oncological, nociceptive or ophthalmic conditions.

8 Claims, No Drawings

FUSED PYRIDINE DERIVATIVES AS KINASE INHIBITORS

This application is a US national phase of International Application No. PCT/GB2009/002504 filed on Oct. 21, 2009, the disclosure of which is incorporated herein by reference in its entirety.

The present invention relates to a class of fused pyridine derivatives, and to their use in therapy. These compounds are selective inhibitors of phosphoinositide 3-kinase (PI3K) enzymes, and are accordingly of benefit as pharmaceutical agents, especially in the treatment of adverse inflammatory, autoimmune, cardiovascular, neurodegenerative, metabolic, oncological, nociceptive and ophthalmic conditions.

The PI3K pathway is implicated in a variety of physiological and pathological functions that are believed to be operative in a range of human diseases. Thus, PI3Ks provide a critical signal for cell proliferation, cell survival, membrane trafficking, glucose transport, neurite outgrowth, membrane ruffling, superoxide production, actin reorganization and chemotaxis (cf. S. Ward et al., *Chemistry & Biology*, 2003, 10, 207-213; and S. G. Ward & P. Finan, *Current Opinion in Pharmacology*, 2003, 3, 426-434); and are known to be involved in the pathology of cancer, and metabolic, inflammatory and cardiovascular diseases (cf. M. P. Wymann et al., *Trends in Pharmacol. Sci.*, 2003, 24, 366-376). Aberrant upregulation of the PI3K pathway is implicated in a wide variety of human cancers (cf. S. Brader & S. A. Eccles, *Tumori*, 2004, 90, 2-8).

The compounds in accordance with the present invention, being potent and selective PI3K inhibitors, are therefore beneficial in the treatment and/or prevention of various human ailments. These include autoimmune and inflammatory disorders such as rheumatoid arthritis, multiple sclerosis, asthma, inflammatory bowel disease, psoriasis and transplant rejection; cardiovascular disorders including thrombosis, cardiac hypertrophy, hypertension, and irregular contractility of the heart (e.g. during heart failure); neurodegenerative disorders such as Alzheimer's disease, Parkinson's disease, Huntington's disease, stroke, amyotrophic lateral sclerosis, spinal cord injury, head trauma and seizures; metabolic disorders such as obesity and type 2 diabetes; oncological conditions including leukaemia, glioblastoma, lymphoma, melanoma, and human cancers of the liver, bone, skin, brain, pancreas, lung, breast, stomach, colon, rectum, prostate, ovary and cervix; pain and nociceptive disorders; and ophthalmic disorders including age-related macular degeneration (ARMD).

In addition, the compounds in accordance with the present invention may be beneficial as pharmacological standards for use in the development of new biological tests and in the search for new pharmacological agents. Thus, the compounds of this invention may be useful as radioligands in assays for detecting compounds capable of binding to human PI3K enzymes.

WO 2008/118454, WO 2008/118455 and WO 2008/118468 describe structurally related series of quinoline and quinoxaline derivatives that are stated to be useful to inhibit the biological activity of human PI3Kδ and to be of use in treating PI3K-mediated conditions or disorders.

Copending international patent application PCT/GB2008/004171, published on 2 Jul. 2009 as WO 2009/081105 (claiming priority from United Kingdom patent applications 0725030.1 and 0815177.1), describes a class of quinoline and quinoxaline derivatives as selective inhibitors of PI3K enzymes that are of benefit in the treatment of adverse inflammatory, autoimmune, cardiovascular, neurodegenerative, metabolic, oncological, nociceptive and ophthalmic conditions.

None of the prior art available to date, however, discloses or suggests the precise structural class of fused pyridine derivatives as provided by the present invention.

The compounds of the present invention are potent and selective PI3K inhibitors having a binding affinity ($IC_{50}$) for the human PI3Kα and/or PI3Kβ and/or PI3Kγ and/or PI3Kδ isoform of 50 μM or less, generally of 20 μM or less, usually of 5 μM or less, typically of 1 μM or less, suitably of 500 nM or less, ideally of 100 nM or less, and preferably of 20 nM or less (the skilled person will appreciate that a lower $IC_{50}$ figure denotes a more active compound). The compounds of the invention may possess at least a 10-fold selective affinity, typically at least a 20-fold selective affinity, suitably at least a 50-fold selective affinity, and ideally at least a 100-fold selective affinity, for the human PI3Kα and/or PI3Kβ and/or PI3Kγ and/or PI3Kδ isoform relative to other human kinases.

The present invention provides a compound of formula (I) or an N-oxide thereof, or a pharmaceutically acceptable salt or solvate thereof:

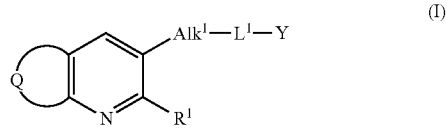

(I)

wherein

Q represents the residue of an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl and triazolyl; or an optionally substituted six-membered heteroaromatic ring selected from pyridinyl, pyridazinyl, pyrimidinyl, pyrazinyl and triazinyl;

$Alk^1$ represents an optionally substituted straight or branched $C_{1-3}$ alkylene chain;

$L^1$ represents oxygen, sulfur, $NR^2$ or a covalent bond;

Y represents an optionally substituted mono- or bicyclic heteroaryl group containing at least one nitrogen atom;

$R^1$ represents a group of formula (a):

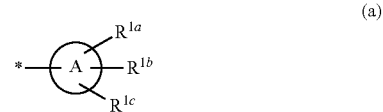

(a)

in which the asterisk (*) represents the point of attachment of the ring A to the remainder of the molecule;

A represents a saturated, partially saturated or unsaturated 4-, 5-, 6- or 7-membered monocyclic ring containing 0, 1, 2, 3 or 4 heteroatoms selected from N, O and S, but containing no more than one O or S atom;

$R^{1a}$, $R^{1b}$ and $R^{1c}$ independently represent hydrogen, halogen, cyano, nitro, oxo, $C_{1-6}$ alkyl, $C_{3-7}$ cycloalkyl, aryl, $C_{3-7}$ heterocycloalkyl (optionally substituted by $C_{1-6}$ alkyl), heteroaryl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkylamino, $C_{2-6}$ alkylcarbonylamino, $C_{2-6}$ alkoxycarbonylamino, $C_{1-6}$alkylsulfonylamino, formyl, $C_{2-6}$ alkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl or di($C_{1-6}$)alkylaminosulfonyl; and $R^2$ represents hydrogen or $C_{1-6}$ alkyl.

Where any of the groups in the compounds of formula (I) above is stated to be optionally substituted, this group may be unsubstituted, or substituted by one or more substituents. Typically, such groups will be unsubstituted, or substituted by one or two substituents.

For use in medicine, the salts of the compounds of formula (I) will be pharmaceutically acceptable salts. Other salts may, however, be useful in the preparation of the compounds of the invention or of their pharmaceutically acceptable salts. Suitable pharmaceutically acceptable salts of the compounds of this invention include acid addition salts which may, for example, be formed by mixing a solution of the compound of the invention with a solution of a pharmaceutically acceptable acid such as hydrochloric acid, sulphuric acid, methanesulphonic acid, fumaric acid, maleic acid, succinic acid, acetic acid, benzoic acid, citric acid, tartaric acid or phosphoric acid. Furthermore, where the compounds of the invention carry an acidic moiety, e.g. carboxy, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The present invention includes within its scope solvates of the compounds of formula (I) above. Such solvates may be formed with common organic solvents, e.g. hydrocarbon solvents such as benzene or toluene; chlorinated solvents such as chloroform or dichloromethane; alcoholic solvents such as methanol, ethanol or isopropanol; ethereal solvents such as diethyl ether or tetrahydrofuran; or ester solvents such as ethyl acetate. Alternatively, the solvates of the compounds of formula (I) may be formed with water, in which case they will be hydrates.

Suitable alkyl groups which may be present on the compounds of the invention include straight-chained and branched $C_{1-6}$ alkyl groups, for example $C_{1-4}$ alkyl groups. Typical examples include methyl and ethyl groups, and straight-chained or branched propyl, butyl and pentyl groups. Particular alkyl groups include methyl, ethyl, n-propyl, isopropyl, n-butyl, sec-butyl, isobutyl, tert-butyl, 2,2-dimethylpropyl and 3-methylbutyl. Derived expressions such as "$C_{1-6}$ alkoxy", "$C_{1-6}$ alkylthio", "$C_{1-6}$ alkylsulphonyl" and "$C_{1-6}$ alkylamino" are to be construed accordingly.

The expression "$C_{1-3}$ alkylene chain" refers to a divalent straight or branched alkylene chain containing 1 to 3 carbon atoms. Typical examples include methylene, ethylene, methylmethylene, ethylmethylene and dimethylmethylene.

Specific $C_{3-7}$ cycloalkyl groups are cyclopropyl, cyclobutyl, cyclopentyl, cyclohexyl and cycloheptyl.

Suitable aryl groups include phenyl and naphthyl, preferably phenyl. Suitable aryl($C_{1-6}$)alkyl groups include benzyl, phenylethyl, phenylpropyl and naphthylmethyl.

Suitable heterocycloalkyl groups, which may comprise benzo-fused analogues thereof, include azetidinyl, tetrahydrofuranyl, dihydrobenzofuranyl, pyrrolidinyl, indolinyl, thiazolidinyl, imidazolidinyl, tetrahydropyranyl, chromanyl, piperidinyl, 1,2,3,4-tetrahydroquinolinyl, 1,2,3,4-tetrahydroisoquinolinyl, piperazinyl, 1,2,3,4-tetrahydroquinoxalinyl, homopiperazinyl, morpholinyl, benzoxazinyl and thiomorpholinyl.

Suitable heteroaryl groups include furyl, benzofuryl, dibenzofuryl, thienyl, benzothienyl, dibenzothienyl, pyrrolyl, indolyl, pyrrolo[2,3-b]pyridinyl, pyrrolo[3,2-c]pyridinyl, pyrazolyl, pyrazolo[1,5-a]pyridinyl, indazolyl, oxazolyl, benzoxazolyl, isoxazolyl, thiazolyl, benzothiazolyl, isothiazolyl, imidazolyl, benzimidazolyl, imidazo[1,2-a]pyridinyl, imidazo[4,5-b]pyridinyl, imidazo[1,2-a]pyrimidinyl, imidazo[1,2-a]pyrazinyl, oxadiazolyl, thiadiazolyl, triazolyl, benzotriazolyl, tetrazolyl, pyridinyl, quinolinyl, isoquinolinyl, pyridazinyl, cinnolinyl, pyrimidinyl, pyrazinyl, quinoxalinyl and chromenyl groups.

The term "halogen" as used herein is intended to include fluorine, chlorine, bromine and iodine atoms, typically fluorine, chlorine or bromine.

Where the compounds of formula (I) have one or more asymmetric centres, they may accordingly exist as enantiomers. Where the compounds of the invention possess two or more asymmetric centres, they may additionally exist as diastereomers. The invention is to be understood to extend to all such enantiomers and diastereomers, and to mixtures thereof in any proportion, including racemates. Formula (I) and the formulae depicted hereinafter are intended to represent all individual stereoisomers and all possible mixtures thereof, unless stated or shown otherwise. In addition, compounds of formula (I) may exist as tautomers, for example keto ($CH_2C=O$) ↔ enol ($CH=CHOH$) tautomers or amide ($NHC=O$) ↔ hydroxyimine ($N=COH$) tautomers. Formula (I) and the formulae depicted hereinafter are intended to represent all individual tautomers and all possible mixtures thereof, unless stated or shown otherwise.

It is to be understood that each individual atom present in formula (I), or in the formulae depicted hereinafter, may in fact be present in the form of any of its naturally occurring isotopes, with the most abundant isotope(s) being preferred. Thus, by way of example, each individual hydrogen atom present in formula (I), or in the formulae depicted hereinafter, may be present as a $^1H$, $^2H$ (deuterium) or $^3H$ (tritium) atom, preferably $^1H$. Similarly, by way of example, each individual carbon atom present in formula (I), or in the formulae depicted hereinafter, may be present as a $^{12}C$, $^{13}C$ or $^{14}C$ atom, preferably $^{12}C$.

In the compounds of formula (I), the moiety Q is defined as representing the residue of an optionally substituted five-membered or six-membered heteroaromatic ring as specified above. From this it is to be understood that the variable Q, when taken together with the two carbon atoms of the pyridine ring to which the Q-containing ring is fused, represents an optionally substituted five-membered or six-membered heteroaromatic ring as specified above.

In one embodiment, the moiety Q in the compounds of formula (I) above represents the residue of an optionally substituted five-membered heteroaromatic ring selected from furyl, thienyl, pyrrolyl, pyrazolyl, oxazolyl, isoxazolyl, thiazolyl, isothiazolyl, imidazolyl, oxadiazolyl, thiadiazolyl, triazolyl and tetrazolyl. In another embodiment, the moiety Q in the compounds of formula (I) above represents the residue of an optionally substituted six-membered heteroaromatic ring selected from pyridinyl, pyridazinyl, pyrimidinyl, pyrazinyl and triazinyl.

Suitably, the moiety Q represents the residue of a thienyl ring, which may be optionally substituted by one or two substitutents. In one embodiment, the moiety Q represents the residue of an unsubstituted thienyl ring.

The five-membered or six-membered heteroaromatic ring of which the moiety Q is the residue may be unsubstituted, or may suitably be substituted, where possible, by one more, typically by one or two, substituents. In one embodiment, this ring is unsubstituted. In another embodiment, this ring is monosubstituted. In a further embodiment, this ring is disubstituted. Examples of typical substituents on the five-membered or six-membered heteroaromatic ring of which the moiety Q is the residue include $C_{1-6}$ alkyl, $C_{3-7}$ cycloalkyl, $C_{3-7}$ cycloalkyl($C_{1-6}$)alkyl, aryl, aryl($C_{1-6}$)alkyl, $C_{3-7}$ heterocycloalkyl, $C_{3-7}$ heterocycloalkyl($C_{1-6}$)alkyl, heteroaryl, heteroaryl($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$)alkylamino, halogen, cyano and trifluoromethyl.

Examples of suitable substituents on the alkylene chain represented by $Alk^1$ include trifluoromethyl, aryl, oxo, hydroxy, $C_{1-6}$ alkoxy, $C_{2-6}$ alkoxycarbonyl($C_{1-6}$)alkoxy, aminocarbonyl($C_{1-6}$)alkoxy, trifluoromethoxy, aminocarbonyl, $C_{1-6}$ alkylaminocarbonyl and di($C_{1-6}$)alkylaminocarbonyl.

Examples of particular substituents on the alkylene chain represented by $Alk^1$ include trifluoromethyl, phenyl, oxo, hydroxy, ethoxy, ethoxycarbonylmethoxy, aminocarbonylmethoxy, trifluoromethoxy, aminocarbonyl, methylaminocarbonyl and dimethylaminocarbonyl.

Typical values of $Alk^1$ include methylene (—$CH_2$—), (methyl)methylene, ethylene (—$CH_2CH_2$—), (ethyl)methylene, (dimethyl)methylene, (methyl)ethylene and (dimethyl)-ethylene, any of which chains may be optionally substituted by one or more substituents. Suitably, such chains are unsubstituted, monosubstituted or disubstituted. Preferably, such chains are unsubstituted or monosubstituted. In one embodiment, such chains are unsubstituted. In another embodiment, such chains are monosubstituted.

Suitable values of $Alk^1$ include —$CH_2$— (methylene), —$CH(CH_3)$— (methyl-methylene) and —$CH(CH_2CH_3)$— (ethylmethylene).

$Alk^1$ typically represents methylene.

Suitably, $L^1$ represents oxygen or sulfur.

In one embodiment, $L^1$ represents oxygen. In another embodiment, $L^1$ represents sulfur. In a further embodiment, $L^1$ represents $NR^2$. In a still further embodiment, $L^1$ represents a covalent bond.

The expression "mono- or bicyclic heteroaryl group containing at least one nitrogen atom" in relation to the group Y refers in particular to a mono- or bicyclic aromatic ring system containing one, two, three or four heteroatoms selected from oxygen, sulfur and nitrogen atoms, with at least one of the heteroatoms being nitrogen. The ring Y may be linked to the group $L^1$ through any available carbon or nitrogen atom. Suitable examples include pyrrolyl, pyridinyl, indolyl, quinolinyl, isoquinolinyl, imidazolyl, pyrazolyl, triazolyl, pyridazinyl, pyrimidinyl, pyrazinyl, triazinyl, indazolyl, benzimidazolyl, furopyridinyl, thienopyridinyl, benzoxazolyl, benzothiazolyl, cinnolinyl, phthalazinyl, quinazolinyl, quinoxalinyl, imidazopyridinyl, pyrazolopyridinyl, purinyl, pyrazolopyrimidinyl, pyrrolopyrimidinyl, triazolopyrimidinyl, pyridopyrimidinyl, pyridopyrazinyl, pyridopyridazinyl, naphthyridinyl and pteridinyl.

Suitably, Y represents optionally substituted pyrimidinyl or optionally substituted purinyl. In one embodiment, Y represents optionally substituted pyrimidinyl. In another embodiment, Y represents optionally substituted purinyl.

Alternative values of Y include pyrrolyl, indolyl, quinolinyl, isoquinolinyl, imidazolyl, pyrazolyl, triazolyl, pyridazinyl, pyrazinyl, triazinyl, indazolyl, benzimidazolyl, furopyridinyl, thienopyridinyl, benzoxazolyl, benzothiazolyl, cinnolinyl, phthalazinyl, quinazolinyl, quinoxalinyl, triazolopyrimidinyl, pyridopyrimidin-4-yl, pyridopyrazinyl, pyridopyridazinyl, naphthyridinyl and pteridinyl, any of which groups may be optionally substituted by one or more substituents. Particular alternative values of Y include quinolinyl, triazinyl, quinoxalinyl and pyridopyrimidin-4-yl, any of which groups may be optionally substituted by one or more substituents.

Examples of optional substituents which may be present on the group Y include one, two or three substituents independently selected from halogen, cyano, nitro, oxo, $C_{1-6}$ alkyl, trifluoromethyl, hydroxy, $C_{1-6}$ alkoxy, difluoromethoxy, trifluoromethoxy, $C_{1-6}$ alkylthio, $C_{1-6}$ alkylsulfinyl, $C_{1-6}$ alkylsulfonyl, amino, $C_{1-6}$ alkylamino, di($C_{1-6}$)alkyl-amino, arylamino, $C_{2-6}$ alkylcarbonylamino, $C_{1-6}$ alkylsulfonylamino, formyl, $C_{2-6}$ alkylcarbonyl, $C_{3-6}$ cycloalkylcarbonyl, $C_{3-6}$ heterocycloalkylcarbonyl, carboxy, $C_{2-6}$ alkoxycarbonyl, aminocarbonyl, $C_{1-6}$ alkylaminocarbonyl, di($C_{1-6}$)alkylaminocarbonyl, aminosulfonyl, $C_{1-6}$ alkylaminosulfonyl and di($C_{1-6}$)alkylaminosulfonyl.

Typical examples of optional substituents on the group Y include $C_{1-6}$ alkyl and amino.

Examples of particular substituents on the group Y include fluoro, chloro, bromo, cyano, nitro, oxo, methyl, isopropyl, trifluoromethyl, hydroxy, methoxy, difluoromethoxy, trifluoromethoxy, methylthio, methylsulfinyl, methylsulfonyl, amino, methylamino, tert-butylamino, dimethylamino, phenylamino, acetylamino, methoxycarbonylamino, methylsulfonylamino, formyl, acetyl, cyclopropylcarbonyl, azetidinylcarbonyl, N-methylazetidinylcarbonyl, pyrrolidinylcarbonyl, N-methylpyrrolidinylcarbonyl, piperidinylcarbonyl, N-methylpiperidinylcarbonyl, piperazinylcarbonyl, N-methylpiperazinylcarbonyl, morpholinylcarbonyl, carboxy, methoxycarbonyl, aminocarbonyl, methylaminocarbonyl, dimethylaminocarbonyl, aminosulfonyl, methylaminosulfonyl and dimethylaminosulfonyl.

Typical examples of particular substituents on the group Y include amino and methyl.

Typical values of Y include purinyl (especially purin-6-yl) and (amino)(methyl)-pyrimidinyl (especially 2-amino-4-methylpyrimidin-6-yl).

Suitable values for the group -$Alk^1$-$L^1$-Y include purin-6-ylthiomethyl and (2-amino-4-methylpyrimidin-6-yl)oxymethyl.

In one embodiment, A is a four-membered monocyclic ring. In another embodiment, A is a five-membered monocyclic ring. In a further embodiment, A is a six-membered monocyclic ring. In an additional embodiment, A is a seven-membered monocyclic ring.

In one embodiment, ring A is fully saturated. In another embodiment, ring A is partially saturated. In a further embodiment, ring A is unsaturated.

In one embodiment, ring A contains no heteroatoms (i.e. it is a carbocyclic ring). In another embodiment, ring A contains one heteroatom selected from N, O and S. In a further embodiment, ring A contains two heteroatoms selected from N, O and S, of which not more than one is O or S. In a still further embodiment, ring A contains three heteroatoms selected from N, O and S, of which not more than one is O or S. In a yet further embodiment, ring A contains four heteroatoms selected from N, O and S, of which not more than one is O or S.

Suitably, ring A represents phenyl.

Typical values of $R^{1a}$, $R^{1b}$ and/or $R^{1c}$ include hydrogen, halogen, $C_{1-6}$ alkyl, trifluoromethyl, $C_{1-6}$ alkoxy, trifluoromethoxy, $C_{2-6}$ alkylcarbonylamino and aryl.

Suitably, $R^{1a}$, $R^{1b}$ and $R^{1c}$ independently represent hydrogen, fluoro, chloro, bromo, cyano, nitro, oxo, methyl, ethyl, isopropyl, cyclopropyl, azetidinyl, N-methylazetidinyl, tetrahydrofuranyl, pyrrolidinyl, N-methylpyrrolidinyl, imidazolidinyl, N-methylimidazolidinyl, tetrahydropyranyl, piperidinyl, N-methylpiperidinyl, piperazinyl, N-methylpiperazinyl, morpholinyl, thiomorpholinyl, phenyl, pyrrolyl, furyl, thienyl, imidazolyl, oxazolyl, isoxazolyl, thiazolyl, isothiazolyl, pyrazolyl, triazolyl, oxadiazolyl, thiadiazolyl, pyridinyl, pyrimidinyl, pyridazinyl, pyrazinyl, tetrazolyl, triazinyl, trifluoromethyl, hydroxy, methoxy, difluoromethoxy, trifluoromethoxy, methylthio, methylsulfinyl, methylsulfonyl, amino, methylamino, dimethylamino, acetylamino, methoxycarbonylamino, methylsulfonylamino, formyl, acetyl, carboxy, methoxycarbonyl, aminocarbonyl, methylaminocarbonyl, dimethylaminocarbonyl, aminosulfonyl, methylaminosulfonyl or dimethylaminosulfonyl.

Typically, $R^{1a}$ represents hydrogen, halogen, $C_{1-6}$ alkyl, trifluoromethyl, $C_{1-6}$ alkoxy, trifluoromethoxy, $C_{2-6}$ alkylcarbonylamino or aryl.

Suitably, $R^{1a}$ represents hydrogen.

Typically, $R^{1b}$ represents hydrogen, halogen or $C_{1-6}$ alkyl.

Suitably, $R^{1b}$ represents hydrogen.

Typically, $R^{1c}$ represents hydrogen.

In a particular embodiment, $R^{1b}$ and $R^{1c}$ both represent hydrogen.

In one embodiment, $R^2$ represents hydrogen. In another embodiment, $R^2$ represents $C_{1-6}$ alkyl, especially methyl.

Suitable values of the group $R^2$ include hydrogen and methyl.

One sub-class of compounds according to the invention is represented by the compounds of formula (IIA) and N-oxides thereof, and pharmaceutically acceptable salts and solvates thereof:

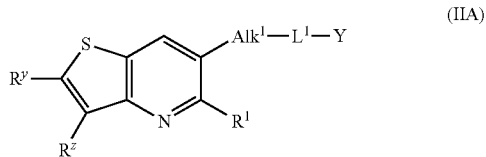

(IIA)

wherein $Alk^1$, $L^1$, Y and $R^1$ are as defined above; and $R^y$ and $R^z$ independently represent hydrogen, $C_{1-6}$ alkyl, $C_{3-7}$ cycloalkyl, $C_{3-7}$ cycloalkyl($C_{1-6}$)alkyl, aryl, aryl($C_{1-6}$) alkyl, $C_{3-7}$ heterocycloalkyl, $C_{3-7}$ heterocycloalkyl-($C_{1-6}$) alkyl, heteroaryl, heteroaryl($C_{1-6}$)alkyl, hydroxy, $C_{1-6}$ alkoxy, $C_{1-6}$ alkylthio, $C_{1-6}$ alkylsulphinyl, $C_{1-6}$ alkylsulphonyl, $C_{2-6}$ alkylcarbonyl, amino, $C_{1-6}$ alkylamino, di($C_{1-6}$)-alkylamino, halogen, cyano or trifluoromethyl.

Suitably, $R^y$ represents hydrogen.

Suitably, $R^z$ represents hydrogen.

Specific novel compounds in accordance with the present invention include each of the compounds whose preparation is described in the accompanying Examples, and pharmaceutically acceptable salts and solvates thereof.

The present invention also provides a pharmaceutical composition which comprises a compound in accordance with the invention as described above, or a pharmaceutically acceptable salt or solvate thereof, in association with one or more pharmaceutically acceptable carriers.

Pharmaceutical compositions according to the invention may take a form suitable for oral, buccal, parenteral, nasal, topical, ophthalmic or rectal administration, or a form suitable for administration by inhalation or insufflation.

For oral administration, the pharmaceutical compositions may take the form of, for example, tablets, lozenges or capsules prepared by conventional means with pharmaceutically acceptable excipients such as binding agents (e.g. pregelatinised maize starch, polyvinylpyrrolidone or hydroxypropyl methyl cellulose); fillers (e.g. lactose, microcrystalline cellulose or calcium hydrogenphosphate); lubricants (e.g. magnesium stearate, talc or silica); disintegrants (e.g. potato starch or sodium glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents, emulsifying agents, non-aqueous vehicles or preservatives. The preparations may also contain buffer salts, flavouring agents, colouring agents or sweetening agents, as appropriate.

Preparations for oral administration may be suitably formulated to give controlled release of the active compound.

For buccal administration, the compositions may take the form of tablets or lozenges formulated in conventional manner.

The compounds of formula (I) may be formulated for parenteral administration by injection, e.g. by bolus injection or infusion. Formulations for injection may be presented in unit dosage form, e.g. in glass ampoules or multi-dose containers, e.g. glass vials. The compositions for injection may take such forms as suspensions, solutions or emulsions in oily or aqueous vehicles, and may contain formulatory agents such as suspending, stabilising, preserving and/or dispersing agents. Alternatively, the active ingredient may be in powder form for constitution with a suitable vehicle, e.g. sterile pyrogen-free water, before use.

In addition to the formulations described above, the compounds of formula (I) may also be formulated as a depot preparation. Such long-acting formulations may be administered by implantation or by intramuscular injection.

For nasal administration or administration by inhalation, the compounds according to the present invention may be conveniently delivered in the form of an aerosol spray presentation for pressurised packs or a nebuliser, with the use of a suitable propellant, e.g. dichlorodifluoromethane, fluorotrichloromethane, dichlorotetrafluoroethane, carbon dioxide or other suitable gas or mixture of gases.

The compositions may, if desired, be presented in a pack or dispenser device which may contain one or more unit dosage forms containing the active ingredient. The pack or dispensing device may be accompanied by instructions for administration.

For topical administration the compounds of use in the present invention may be conveniently formulated in a suitable ointment containing the active component suspended or dissolved in one or more pharmaceutically acceptable carriers. Particular carriers include, for example, mineral oil, liquid petroleum, propylene glycol, polyoxyethylene, polyoxypropylene, emulsifying wax and water. Alternatively, the compounds of use in the present invention may be formulated in a suitable lotion containing the active component suspended or dissolved in one or more pharmaceutically acceptable carriers. Particular carriers include, for example, mineral oil, sorbitan monostearate, polysorbate 60, cetyl esters wax, cetearyl alcohol, benzyl alcohol, 2-octyldodecanol and water.

For ophthalmic administration the compounds of use in the present invention may be conveniently formulated as micronized suspensions in isotonic, pH-adjusted sterile saline, either with or without a preservative such as a bactericidal or fungicidal agent, for example phenylmercuric nitrate, benzylalkonium chloride or chlorhexidine acetate. Alternatively, for ophthalmic administration compounds may be formulated in an ointment such as petrolatum.

For rectal administration the compounds of use in the present invention may be conveniently formulated as suppositories. These can be prepared by mixing the active component with a suitable non-irritating excipient which is solid at room temperature but liquid at rectal temperature and so will melt in the rectum to release the active component. Such materials include, for example, cocoa butter, beeswax and polyethylene glycols.

The quantity of a compound of use in the invention required for the prophylaxis or treatment of a particular condition will vary depending on the compound chosen and the condition of the patient to be treated. In general, however, daily dosages may range from around 10 ng/kg to 1000 mg/kg, typically from 100 ng/kg to 100 mg/kg, e.g. around 0.01 mg/kg to 40 mg/kg body weight, for oral or buccal administration, from around 10 ng/kg to 50 mg/kg body weight for parenteral administration, and from around 0.05 mg to around 1000 mg, e.g. from around 0.5 mg to around 1000 mg, for nasal administration or administration by inhalation or insufflation.

The compounds of formula (I) above may be prepared by a process which comprises reacting a compound of formula (III) with a compound of formula (IV):

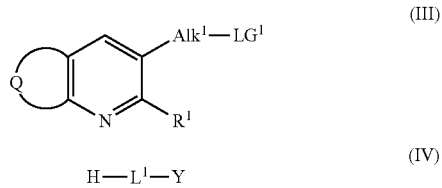

(III)

H—L¹—Y (IV)

wherein Q, Alk¹, L¹, Y and R¹ are as defined above, and LG¹ represents a suitable leaving group.

The leaving group LG¹ is typically a halogen atom, e.g. bromo.

The reaction is conveniently effected at ambient or elevated temperature in a suitable solvent, e.g. N,N-dimethylformamide or acetonitrile. The reaction may be performed in the presence of a suitable base, e.g. an inorganic base such as potassium carbonate, cesium carbonate, sodium hydride or aqueous sodium hydroxide.

The intermediates of formula (III) above wherein LG¹ is bromo may be prepared from a compound of formula (V):

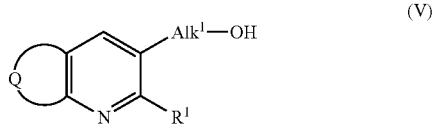

(V)

wherein Q, Alk¹ and R¹ are as defined above; by bromination.

The reaction is conveniently effected by stirring compound (V) with an appropriate brominating agent, e.g. phosphorus tribromide, in a suitable solvent, e.g. a halogenated hydrocarbon such as dichloromethane.

Alternatively, the intermediates of formula (III) above wherein Alk¹ represents methylene and LG¹ is bromo may be prepared from a compound of formula (VI):

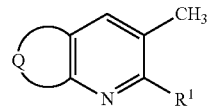

(VI)

wherein Q and R¹ are as defined above; by bromination.

The reaction is conveniently effected at an elevated temperature in a suitable solvent, e.g. a halogenated solvent such as carbon tetrachloride, in the presence of a suitable brominating agent, e.g. N-bromosuccinimide, typically in the presence of a catalyst such as benzoyl peroxide.

In another procedure, the compounds of formula (I) wherein L¹ represents oxygen may be prepared by a process which comprises reacting a compound of formula (V) as defined above with a compound of formula LG²-Y, in which Y is as defined above and LG² represents a suitable leaving group.

The leaving group LG² is typically a halogen atom, e.g. chloro.

The reaction is conveniently effected by stirring compound (V) with a compound LG²-Y in a suitable solvent, e.g. N,N-dimethylformamide, typically under basic conditions, e.g. in the presence of an inorganic base such as sodium hydride.

In another procedure, the compounds of formula (I) wherein L¹ represents sulfur may be prepared by a process which comprises reacting a compound of formula LG²-Y with a compound of formula (VII):

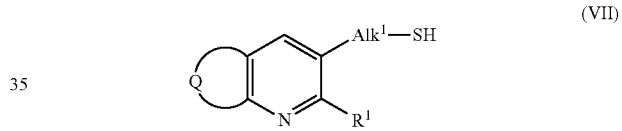

(VII)

wherein Q, Alk¹, Y, R¹ and LG² are as defined above.

The reaction is conveniently effected by stirring compound (VII) with a compound LG²-Y in a suitable solvent, e.g. a lower alkanol such as methanol, typically under basic conditions, e.g. in the presence of an alkali metal alkoxide such as sodium methoxide.

The intermediates of formula (VII) may typically be prepared by treating a suitable compound of formula (III) above with thiolacetic acid; followed by treatment of the resulting compound with a base, e.g. an alkali metal alkoxide such as sodium methoxide.

In another procedure, the compounds of formula (I) wherein L¹ represents NR² may be prepared by a process which comprises reacting a compound of formula LG²-Y with a compound of formula (VIII):

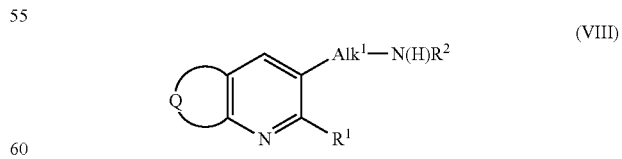

(VIII)

wherein Q, Alk¹, Y, R¹, R² and LG² are as defined above.

The reaction is conveniently effected at an elevated temperature in a suitable solvent, e.g. tetrahydrofuran, n-butanol or 1-methyl-2-pyrrolidinone (NMP). The reaction may be performed in the presence of a suitable base, e.g. an organic base such as N,N-diisopropylethylamine.

The intermediates of formula (VIII) wherein $R^2$ represents hydrogen may be prepared by treating a suitable compound of formula (III) above with potassium phthalimide; followed by treatment of the resulting compound with hydrazine. Alternatively, they may be prepared by treating a suitable compound of formula (III) above with sodium azide; followed by treatment of the resulting compound with triphenylphosphine.

In an additional procedure, the compounds of formula (I) wherein $Alk^1$ represents methylene and $L^1$ represents $NR^2$ may be prepared by a process which comprises reacting a compound of formula Y—N(H)$R^2$ with a compound of formula (IX):

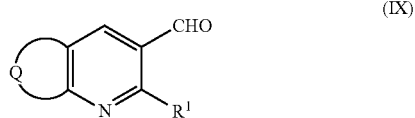

wherein Q, Y, $R^1$ and $R^2$ are as defined above; under reducing conditions.

The reaction is conveniently effected by stirring compound (IX) with a compound Y—N(H)$R^2$ at an elevated temperature in a suitable solvent, e.g. a cyclic ether such as tetrahydrofuran, in the presence of a reducing agent. A suitable reducing agent comprises a mixture of di-n-butyltin dichloride and phenylsilane.

The intermediates of formula (VIII) wherein $Alk^1$ represents methylene and $R^2$ represents $C_{1-6}$ alkyl, e.g. methyl, may be prepared by treating a suitable compound of formula (IX) above with a $C_{1-6}$ alkylamine, e.g. methylamine, in the presence of titanium(IV) n-propoxide and a base, e.g. an organic base such as N,N-diisopropylamine; followed by treatment of the resulting compound with a reducing agent, e.g. sodium triacetoxyborohydride.

The intermediates of formula (V) wherein $Alk^1$ represents methylene may be prepared from the corresponding compound of formula (IX) by treatment with a reducing agent, e.g. sodium borohydride.

Where they are not commercially available, the starting materials of formula (IV), (VI) and (IX) may be prepared by methods analogous to those described in the accompanying Examples, or by standard methods well known from the art. By way of illustration, the group $R^1$ may be introduced into the molecule by standard techniques, such as Suzuki conditions.

It will be understood that any compound of formula (I) initially obtained from any of the above processes may, where appropriate, subsequently be elaborated into a further compound of formula (I) by techniques known from the art. By way of illustration, a compound of formula (I) wherein the moiety Y is substituted by a halogen atom, e.g. chloro, may be converted into the corresponding compound wherein Y is substituted by amino (—NH$_2$) by treatment with ammonia. Similarly, a compound of formula (I) wherein the moiety Y is substituted by a halogen atom, e.g. chloro, may be converted into the corresponding compound wherein Y is substituted by $C_{1-6}$ alkylamino (e.g. methylamino or tert-butylamino), di($C_{1-6}$)alkylamino (e.g. dimethylamino) or arylamino (e.g. phenyl-amino) by treatment with the appropriate $C_{1-6}$ alkylamine (e.g. methylamine or tert-butylamino), di($C_{1-6}$)alkylamine (e.g. dimethylamine) or arylamine (e.g. aniline) respectively.

Where a mixture of products is obtained from any of the processes described above for the preparation of compounds according to the invention, the desired product can be separated therefrom at an appropriate stage by conventional methods such as preparative HPLC; or column chromatography utilising, for example, silica and/or alumina in conjunction with an appropriate solvent system.

Where the above-described processes for the preparation of the compounds according to the invention give rise to mixtures of stereoisomers, these isomers may be separated by conventional techniques. In particular, where it is desired to obtain a particular enantiomer of a compound of formula (I) this may be produced from a corresponding mixture of enantiomers using any suitable conventional procedure for resolving enantiomers. Thus, for example, diastereomeric derivatives, e.g. salts, may be produced by reaction of a mixture of enantiomers of formula (I), e.g. a racemate, and an appropriate chiral compound, e.g. a chiral base. The diastereomers may then be separated by any convenient means, for example by crystallisation, and the desired enantiomer recovered, e.g. by treatment with an acid in the instance where the diastereomer is a salt. In another resolution process a racemate of formula (I) may be separated using chiral HPLC. Moreover, if desired, a particular enantiomer may be obtained by using an appropriate chiral intermediate in one of the processes described above. Alternatively, a particular enantiomer may be obtained by performing an enantiomer-specific enzymatic biotransformation, e.g. an ester hydrolysis using an esterase, and then purifying only the enantiomerically pure hydrolysed acid from the unreacted ester antipode. Chromatography, recrystallisation and other conventional separation procedures may also be used with intermediates or final products where it is desired to obtain a particular geometric isomer of the invention.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3$^{rd}$ edition, 1999. The protecting groups may be removed at any convenient subsequent stage utilising methods known from the art.

The following Examples illustrate the preparation of compounds according to the invention.

The compounds in accordance with this invention potently inhibit the activity of human PI3Kα and/or PI3Kβ and/or PI3Kγ and/or PI3Kδ.

Enzyme Inhibition Assays

Measurement of the ability of compounds to inhibit the lipid kinase activity of the four class 1 PI3 kinase isoforms (α, β, γ and δ) was performed using a commercially available homogeneous time-resolved fluorescence assay as described by Gray et al., *Anal. Biochem.*, 2003, 313, 234-245, according to the manufacturer's instructions (Upstate). All assays were performed at 2 μM ATP and a concentration of purified class 1 PI3 kinase known to generate product within the linear range of the assay. Dilutions of inhibitor in DMSO were added to the assay and compared with assays run in the presence of 2% (v/v) DMSO alone (100% activity). The concentration of inhibitor required to inhibit the enzyme activity by 50% is quoted as the IC$_{50}$.

When tested in the above assay, the compounds of the accompanying Examples were all found to possess IC$_{50}$ values for inhibition of activity of human PI3Kα and/or PI3Kβ and/or PI3Kγ and/or PI3Kδ of 50 μM or better.

EXAMPLES

Abbreviations
DCM: dichloromethane DME: ethylene glycol dimethyl ether
DMF: N,N-dimethylformamide DMSO: dimethylsulfoxide
Et$_2$O: diethyl ether EtOAc: ethyl acetate
MeCN: acetonitrile MeOH: methanol
Pd(PPh$_3$)$_4$: tetrakis(triphenylphosphine)palladium(0)
br: broad h: hour
M: mass r.t.: room temperature
RT: retention time SiO$_2$: silica
ES+: electrospray positive ionisation
HPLC: high performance liquid chromatography
LCMS: liquid chromatography mass spectrometry
Analytical Conditions All NMRs were obtained either at 300 MHz or 400 MHz.

Compounds were named with the aid of Beilstein Autonom.

All reactions involving air- or moisture-sensitive reagents were performed under a nitrogen atmosphere using dried solvents and glassware. Degassing was performed by bubbling nitrogen through the reaction mixture.

Compounds that required preparative HPLC were purified using Method 1.

Method 1: Phenomenex Luna C18(2) 250×21.2 mm, 5 µm column. Mobile phase A: 99.92% water, 0.08% formic acid. Mobile phase B: 99.92% MeCN, 0.08% formic acid. Gradient program (flow rate 25.0 mL/min), column temperature: ambient, variable gradient.

The analytical method used for LCMS was Method 2 below.

Method 2: Phenomenex Luna C18(2) 100×4.6 mm, 5 µm column. Mobile phase A: 99.92% water, 0.08% formic acid. Mobile phase B: 99.92% MeCN, 0.08% formic acid.

Gradient program (flow rate 3.0 mL/min, column temperature 35° C.):

| Time | A % | B % |
|------|-----|-----|
| 0.00 | 95.0 | 5.0 |
| 4.40 | 5.0 | 95.0 |
| 5.30 | 5.0 | 95.0 |
| 5.32 | 95.0 | 5.0 |
| 6.50 | 95.0 | 5.0 |

Intermediate 1

5-Phenylthieno[3,2-b]pyridine-6-carbaldehyde

To a solution of 5-chlorothieno[3,2-b]pyridine-6-carbaldehyde (396 mg, 2.01 mmol) in DME/water (10 mL/2 mL) was added phenylboronic acid (306 mg, 2.51 mmol), K$_2$CO$_3$ (833 mg, 6.03 mmol) and Pd(PPh$_3$)$_4$ (116 mg, 0.1 mmol). The mixture was degassed before being heated in a sealed tube at 100° C. for 5 h. The reaction mixture was allowed to cool to room temperature, diluted with EtOAc (25 mL), washed with water (2×10 mL) and washed with brine (10 mL). The organic layer was separated, dried (MgSO$_4$), filtered and the solvent removed in vacuo. The residue was purified by column chromatography (SiO$_2$, 0-40% EtOAc in heptane) to give the title compound (416 mg, 86%) as a white solid. $\delta_H$ (CDCl$_3$) 10.15 (s, 1H), 8.88 (s, 1H), 8.97 (d, J 6 Hz, 1H), 7.69 (d, J 6 Hz, 1H), 7.50-7.65 (m, 5H). LCMS (ES+) 240.2 (M+H)$^+$, RT 3.46 minutes (Method 2).

Intermediate 2

(5-Phenylthieno[3,2-b]pyridin-6-yl)methanol

To a solution of Intermediate 1 (416 mg, 1.74 mmol) in DCM/MeOH (7.5 mL/2.5 mL) was added NaBH$_4$ (87 mg, 2.26 mmol) and the mixture stirred at r.t. for 2 h. 2M Aqueous NaOH (5 mL) was added and the organic phase separated. The aqueous layer was extracted with DCM (5 mL). The organic layers were combined, washed with water (2×5 mL), dried (MgSO$_4$), filtered and concentrated in vacuo to give the title compound (416 mg, 99%) as a white solid. $\delta_H$ (CDCl$_3$) 8.28 (s, 1H), 7.70 (d, J 6 Hz, 1H), 7.53 (d, J 6 Hz, 1H), 7.30-7.45 (m, 5H), 4.57 (s, 2H), 3.83 (br s, 1H). LCMS (ES+) 242.2 (M+H)$^+$, RT 2.17 minutes (Method 2).

Intermediate 3

6-Bromomethyl-5-phenylthieno[3,2-b]pyridine

To a solution of Intermediate 2 (416 mg, 1.73 mmol) in DCM (10 mL) was added phosphorus tribromide (0.81 mL, 8.63 mmol) and the reaction mixture was stirred at r.t. for 5 h. The mixture was neutralised by the cautious addition of saturated aqueous NaHCO$_3$ solution and the aqueous layer extracted with DCM (2×15 mL). The combined organic layers were washed with water (15 mL), separated, dried (MgSO$_4$), filtered and concentrated in vacuo to give the title compound (586 mg, quantitative) as a white solid. $\delta_H$ (CDCl$_3$) 8.39 (s, 1H), 7.83 (d, J 6 Hz, 1H), 7.65-7.69 (m, 2H), 7.60 (d, J 6 Hz, 1H), 7.44-7.55 (m, 3H), 4.63 (s, 2H). LCMS (ES+) 304.1, 306.1 (M+H)$^+$, RT 3.94 minutes (Method 2).

Example 1

6-(5-Phenylthieno[3,2-b]pyridin-6-ylmethylsulfanyl)-9H-purine

To a solution of Intermediate 3 (293 mg, 0.96 mmol) in dry DMF (15 mL) under nitrogen at r.t. was added K$_2$CO$_3$ (140 mg, 1.01 mmol) and 6-mercaptopurine (172 mg, 1.01 mmol). The reaction mixture was stirred at r.t. for 5 h and partitioned between EtOAc (50 mL) and water (20 mL). A white precipitate formed in the aqueous layer and this was collected by filtration, washed with water, washed with Et$_2$O and dried in a vacuum oven to give the title compound (183 mg, 52%) as a white solid. $\delta_H$ (DMSO-d$_6$) 13.50 (br s, 1H), 8.73 (s, 1H), 8.64 (s, 1H), 8.41 (s, 1H), 8.18 (d, J 6 Hz, 1H), 7.43-7.68 (m, 6H), 4.77 (s, 2H). LCMS (ES+) 376.1 (M+H)$^+$, RT 2.71 minutes (Method 2).

Example 2

4-Methyl-6-(5-phenylthieno[3,2-b]pyridin-6-ylmethoxy)pyrimidin-2-ylamine

To a suspension of sodium hydride (48 mg, 1.20 mmol, 60% dispersion in mineral oil) was added 2-amino-4-hydroxy-6-methylpyrimidine (133 mg, 1.06 mmol). After stirring at r.t. for 0.5 h, addition of a solution of Intermediate 3 (293 mg, 0.96 mmol) in DMF (10 mL) took place. The reaction mixture was heated at 100° C. for 2 h. Water (10 mL) was added and mixture extracted with EtOAc (50 mL). The organic layer was washed with water (3×25 mL), washed with brine (25 mL), separated, dried (MgSO$_4$), filtered and the solvent removed in vacuo. Purification was by preparative HPLC (Method 1). The fractions containing the desired product were combined, neutralised with aqueous NaHCO$_3$ solution and concentrated in vacuo. The residue was redissolved in water (20 mL) and extracted with DCM (2×15 mL). The organic layers were combined, washed with water (10 mL), separated, dried (MgSO$_4$), filtered and the solvent removed in vacuo to give the title compound (34 mg, 9%) as a white solid. $\delta_H$ (CDCl$_3$) 8.40 (s, 1H), 7.80 (d, J 6 Hz, 1H), 7.58-7.62 (m, 3H), 7.42-7.50 (m, 3H), 6.00 (s, 1H), 5.40 (s, 2H), 4.90 (s, 2H), 2.26 (s, 3H). LCMS (ES+) 349.1 (M+H)$^+$, RT 1.93 minutes (Method 2).

The invention claimed is:

1. A compound represented by formula (IIA) or an N-oxide thereof, or a pharmaceutically acceptable salt or solvate thereof:

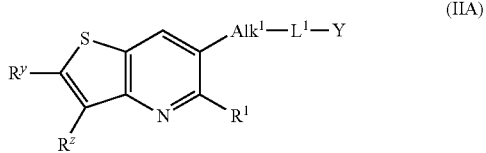

(IIA)

wherein

Alk$^l$ represents an optionally substituted straight or branched C$_{1-3}$ alkylene chain;

L$^1$ represents oxygen, sulfur, NR$^2$ or a covalent bond;

Y represents an optionally substituted mono- or bicyclic heteroaryl group containing at least one nitrogen atom;

R$^1$ represents a group of formula (a):

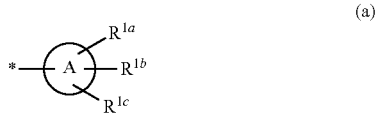

(a)

in which the asterisk (*) represents the point of attachment of the ring A to the remainder of the molecule;

A represents a saturated, partially saturated or unsaturated 4-, 5-, 6- or 7-membered monocyclic ring containing 0, 1, 2, 3 or 4 heteroatoms selected from N, O and S, but containing no more than one O or S atom;

R$^{1a}$, R$^{1b}$ and R$^{1c}$ independently represent hydrogen, halogen, cyano, nitro, oxo, C$_{1-6}$ alkyl, C$_{3-7}$ cycloalkyl, aryl, C$_{3-7}$ heterocycloalkyl (optionally substituted by C$_{1-6}$ alkyl), heteroaryl, trifluoromethyl, hydroxy, C$_{1-6}$ alkoxy, difluoromethoxy, trifluoromethoxy, C$_{1-6}$ alkylthio, C$_{1-6}$ alkylsulfinyl, C$_{1-6}$ alkylsulfonyl, amino, C$_{1-6}$ alkylamino, di(C$_{1-6}$)alkylamino, C$_{2-6}$ alkylcarbonylamino, C$_{2-6}$ alkoxycarbonylamino, C$_{1-6}$ alkylsulfonylamino, formyl, C$_{2-6}$ alkylcarbonyl, carboxy, C$_{2-6}$ alkoxycarbonyl, aminocarbonyl, C$_{1-6}$ alkylaminocarbonyl, di(C$_{1-6}$) alkylaminocarbon, aminosulfonyl, C$_{1-6}$ alkylaminosulfonyl or di (C$_{1-6}$) alky laminosulfonyl;

R$^2$ represents hydrogen or C$_{1-6}$ alkyl; and

R$^y$ and R$^z$ independently represent hydrogen, C$_{1-6}$ alkyl, C$_{3-7}$ cycloalkyl, C$_{3-7}$ cycloalkyl(C$_{1-6}$)alkyl, aryl, aryl (C$_{1-6}$)alkyl, C$_{3-7}$ heterocycloalkyl, C$_{3-7}$ heterocycloalkyl-(C$_{1-6}$) alkyl, heteroaryl, heteroaryl(C$_{1-6}$)alkyl, hydroxy, C$_{1-6}$ alkoxy, C$_{1-6}$ alkylthio, C$_{1-6}$ alkylsulphinyl, C$_{1-6}$ alkylsulphonyl, C$_{2-6}$ alkylcarbonyl, amino, C$_{1-6}$ alkylamino, di(C$_{1-6}$) -alkylamino, halogen, cyano or trifluoromethyl.

2. A compound as claimed in claim 1 wherein Alk$^1$ represents methylene, (methyl)methylene or (ethyl)methylene.

3. A compound as claimed in claim 1 wherein L$^1$ represents oxygen or sulfur.

4. A compound as claimed in claim 1 wherein Y represents quinolinyl, pyrimidinyl, triazinyl, quinoxalinyl, purinyl or pyridopyrimidin-4-yl, any of which groups may be optionally substituted by one or more substituents.

5. A compound as claimed in claim 1 wherein Y is unsubstituted, or substituted by one or more substituents selected from C$_{1-6}$ alkyl and amino 6. A compound as claimed in claim 1 wherein R$^1$ represents phenyl.

7. A compound selected from the group consisting of 6-(5-Phenylthieno[3,2-b]pyridin-6-ylmethylsulfanyl)-9H-purine, and 4-Methyl-6-(5-phenylthieno[3,2-b]pyridin-6-ylmethoxy)pyrimidin-2-ylamine.

8. A pharmaceutical composition comprising a compound of formula (I) as defined in claim 1 or an N-oxide thereof, or a pharmaceutically acceptable salt or solvate thereof, in association with a pharmaceutically acceptable carrier.

* * * * *